(12) United States Patent
Darling et al.

(10) Patent No.: US 7,204,691 B2
(45) Date of Patent: Apr. 17, 2007

(54) ELASTOMERIC ORTHODONTIC LIGATOR

(76) Inventors: Steven Darling, 4535 Coquina Rd., Ocean Ridge, FL (US) 33435-7359; Janis Darling, 4535 Coquina Rd., Ocean Ridge, FL (US) 33435-7359

( * ) Notice: Subject to any disclaimer, the term of this patent is extended or adjusted under 35 U.S.C. 154(b) by 55 days.

(21) Appl. No.: 11/105,038

(22) Filed: Apr. 12, 2005

(65) Prior Publication Data

US 2006/0228663 A1 Oct. 12, 2006

(51) Int. Cl.
*A61C 7/00* (2006.01)

(52) U.S. Cl. ........................................ 433/11

(58) Field of Classification Search ............... 433/11, 433/15, 13, 18
See application file for complete search history.

(56) References Cited

U.S. PATENT DOCUMENTS

| | | | | |
|---|---|---|---|---|
| 3,758,947 A | * | 9/1973 | Kesling | 433/18 |
| 4,687,441 A | * | 8/1987 | Klepacki | 433/8 |
| 5,378,146 A | * | 1/1995 | Sterrett | 433/11 |
| 6,254,383 B1 | * | 7/2001 | White | 433/18 |
| 2003/0008259 A1 | * | 1/2003 | Kuo et al. | 433/6 |

* cited by examiner

*Primary Examiner*—Melba Bumgarner
(74) *Attorney, Agent, or Firm*—Robert M. Downey, PA

(57) ABSTRACT

A ligation device for use with an orthodontic appliance having individual brackets attached to a patient's teeth and an arch wire received within a slot of each of the brackets. The ligator is formed of an elastomeric material and includes an O-ring portion surrounding a central area and an integral membrane covering the central area. The O-ring portion is adapted to stretch over hook shaped projections on the bracket for producing a continually acting tractive force that urges the arch wire against the bracket. The membrane has a diameter equal to or less than the outermost diameter of the O-ring portion so that, when the ligator is attached to the bracket, the membrane is pulled tight and the prongs and slot are concealed from view. An ornamental design or indicia on the outer face of the membrane is visibly exposed to provide an aesthetically appealing and fashionable appearance. The ligator is provided in multiple colors, with any of a variety of ornamental designs, symbols and/or indicia on the outer membrane face, for selective arrangement and exchange according to patient preference.

12 Claims, 2 Drawing Sheets

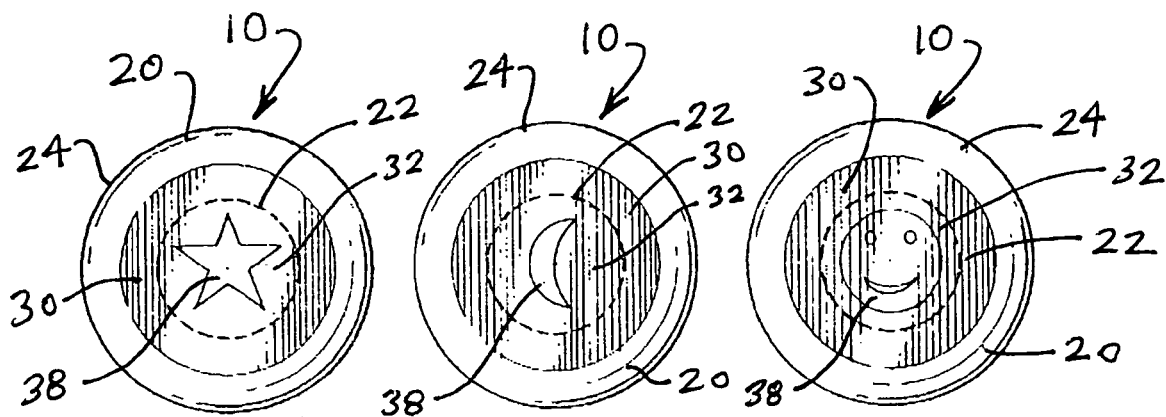
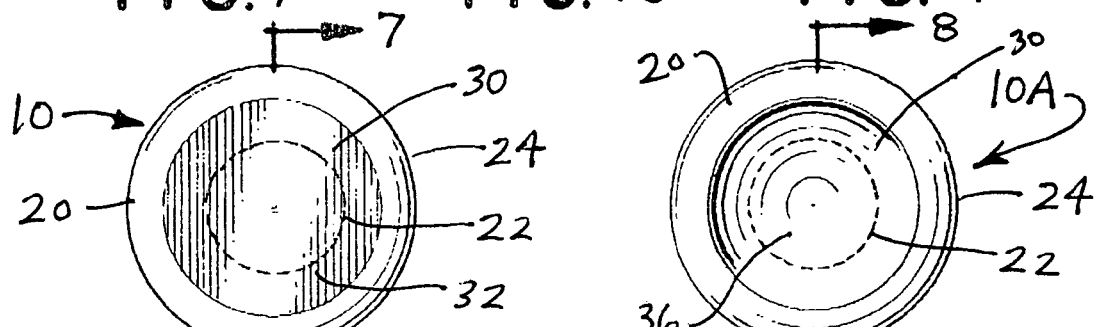
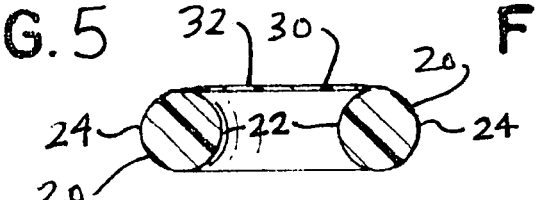
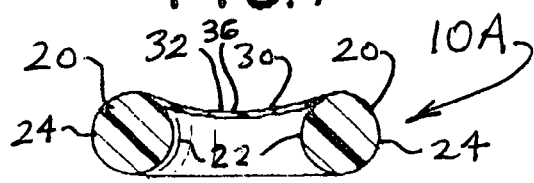

ELASTOMERIC ORTHODONTIC LIGATOR

BACKGROUND OF THE INVENTION

1. Field of the Invention

This invention relates to orthodontic appliances and, more particularly, to elastomeric ligation devices for attachment to brackets on a patient's teeth in order to produce a tractive force urging an arch wire against the brackets.

2. Discussion of the Related Art

Elastomeric O-ring orthodontic ligators are well known and have been used extensively in the field of Orthodontics for over thirty years. Sometimes referred to as A-LASTICS or SPEEDOS, O-ring ligators are usually formed of latex and are adapted to stretch over and secure under the hook shaped projections of individual brackets attached to the teeth of a patient as part of an orthodontic appliance. Each bracket is provided with a lateral slot formed between the oppositely oriented hook shaped projections. The brackets are attached to the patient's teeth in a manner which aligns the slots for receipt of an arch wire therethrough in interjoining relation between the adjacently arranged brackets. The O-ring ligators stretch over and attach under the projecting prongs, crossing over the outer side of the arch wire, to produce a continually acting tractive force which urges the arch wire inwardly against the brackets, and hence the teeth, to assist in correction of tooth positioning.

Early examples of O-ring type ligators are seen in U.S. Pat. No. 3,530,583 to Klein, et al. and U.S. Pat. No. 3,758,947 to Kessling.

For many years, orthodontic appliances were considered to be unattractive and, to some extent, unsightly, causing many orthodontic patients to feel embarrassed by their personal appearance. However, the relatively recent introduction of multi-color O-ring ligators has led to somewhat of a fashion craze, particular among children who are required to wear an orthodontic appliance. The ability to select and wear any particular color ligator, or multiple colors, including vibrant neon colors, is extremely appealing to younger children and teenagers. For instance, orthodontic patients can select ligators of multiple colors to coincide with a particular holiday, such as red, white and blue for Independence day or black and orange for Halloween. Sports fans may choose to wear colors of their favorite team. And, because latex O-ring ligators need to be changed frequently, usually every six to eight weeks, the patient can regularly change the color and/or color pattern to suit their preference. This ability to select and interchange colors has provided an element of fun and fashion to the otherwise mundane experience of wearing an orthodontic device.

Notwithstanding the visual benefits and general appeal of multi-color O-ring ligators in the field of orthodontics, there remains a need to enhance the overall appearance of the orthodontic appliance without altering the structure, performance and overall function of the appliance. More particularly, there remains a need to improve the appearance of orthodontic appliances, while keeping with the fashion trend generated by the introduction of multi-color O-ring ligators, by covering a substantial portion of the brackets, and particularly, the prongs and slots, and displaying an ornamental design, symbol, trademark or other indicia. This would allow the patient to not only wear one or more colors on their appliance, but to also hide the brackets from view and, instead, display an ornamental design (e.g. a star, lightening bolt, flower, etc.) or some other indicia such as sports related symbols (e.g. baseball, football, basketball) or a team or school logo.

OBJECTS AND ADVANTAGES OF THE INVENTION

With the foregoing in mind, it is a primary object of the present invention to provide a ligation device for use with an orthodontic appliance having individual brackets attached to a patient's teeth and an arch wire received within a slot of each of the brackets, and wherein the ligation device is formed of an elastomeric material and includes an O-ring portion and an integral membrane having a diameter equal to or less than the outer most diameter of the O-ring portion, and wherein the membrane is adapted to cover the bracket to provide an aesthetically appealing and fashionable appearance.

It is still a further object of the present invention to provide an elastomeric ligator which is adapted for use with an existing orthodontic appliance which uses brackets and an arch wire, and wherein the ligator is structured to cover the bracket and visibly expose an outer face of a membrane portion to provide an aesthetically appealing and fashionable appearance.

It is still a further object of the present invention to provide a ligator device, as set forth above, which is provided in multiple colors.

It is still a further object of the present invention to provide a ligator device, as set forth above, wherein an outer face of the membrane portion is provided with one or more designs, symbols and/or indicia according to patient preference.

These and other objects and advantages of the present invention are more readily apparent with reference to the following detailed description and accompanying drawings.

SUMMARY OF THE INVENTION

The present invention is directed to a ligation device which is specifically adapted for use with an orthodontic appliance of the type which includes individual brackets attached to a patient's teeth and an arch wire that is received within a slot of each of the brackets. The ligation device is formed of an elastomeric material, such as latex, and includes an O-ring portion surrounding a central area and an integral membrane covering the central area. The O-ring portion is sized and structured to stretch over hook shaped projections on the bracket for producing a continually acting tractive force that urges the arch wire against the bracket. The membrane has a diameter equal to or less than the outermost diameter of the O-ring portion so that, when the ligator is attached to the bracket, pulled tight and the prongs and slot are concealed from view. Accordingly, the membrane portion serves as a cover over the bracket, while providing an outer exposed face for application of any select ornamental design, symbol, trademark and/or other indicia thereon. When attached to the brackets, the outer faces of each of the ligator devices is exposed to reveal the one or more colors on the ligator devices. Additionally, the select design, symbol or indicia on the outer face provides for additional novelty and independent selection by the patient.

BRIEF DESCRIPTION OF THE DRAWINGS

For a fuller understanding of the nature of the present invention, reference should be made to the following detailed description taken in conjunction with the accompanying drawings in which:

FIG. 5 is a top plan view of the elastomeric ligation device in accordance with a first preferred embodiment thereof;

FIG. 6 is a top plan view of the elastomeric ligation device of the present invention, in accordance with a second preferred embodiment thereof;

FIG. 7 is a cross-sectional view taken along the line indicated as 7—7 in FIG. 5;

FIG. 8 is a cross-sectional view taken along the line indicated as 8—8 in FIG. 6;

FIG. 9 is a top plan view of the elastomeric ligation device showing a star design applied to the front face of the membrane thereof;

FIG. 10 is a top plan view of the elastomeric ligation device showing a half-moon design applied to the front face of the membrane thereof; a FIG. 11 is a top plan view of the elastomeric ligation device showing a smiley face design applied to the front face of the membrane thereof.

Like reference numerals refer to like parts throughout the several views of the drawings.

DETAILED DESCRIPTION OF THE PREFERRED EMBODIMENTS

Figure 1:
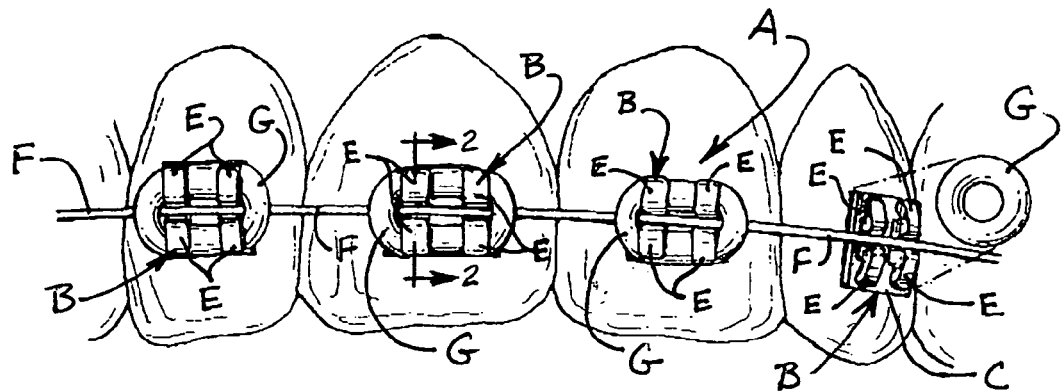
FIG. 1 is a front perspective view showing an arrangement of teeth with a prior art orthodontic appliance installed with the use of O-ring ligators.
Figure 2:
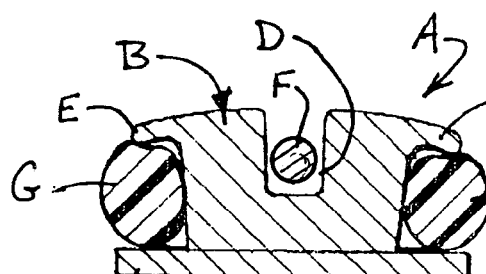
FIG. 2 is a cross-sectional view taken along the line indicated as 2—2 in FIG. 1.

Referring initially to FIGS. 1 and 2, a prior art orthodontic appliance is shown and indicated as A. Specifically, FIG. 1 illustrates an arrangement of four adjacent upper teeth of a patient fitted with the prior art orthodontic appliance A which uses individual brackets B bonded to the outer facing surface of each of the adjacent teeth. Each of the brackets B includes a base C and a lateral slot D formed between oppositely oriented hook shaped projections or prongs E. The brackets B are bonded to the patient's teeth in a manner which aligns the slots D for receipt of an arch wire F therethrough in interjoining relation between the adjacently arranged brackets. The prior art appliance uses elastomeric O-ring ligators G that have an open center. As shown in FIGS. 1 and 2, the elastomeric O-ring ligators G are attached to each bracket. More specifically, the O-ring ligators G stretch over and attach under the projecting prongs E, crossing over the outer side of the arch wire F, to produce a continually acting tractive force which urges the arch wire inwardly against the brackets B, and hence the teeth, to assist in correction of tooth positioning. FIG. 2 is a cross-section that illustrates the fastening of the O-ring ligator G under the projecting prongs E of the bracket B with the arch wire F maintained within the slot D of the bracket. The orthodontic appliance A shown in FIGS. 1 and 2, and the use of elastomeric O-ring ligators G to secure the arch wire within the bracket, is well known in the field of orthodontics and has been in use for many years.

As seen in FIG. 1, the attachment of the O-ring ligator G to the bracket B in the prior art orthodontic appliance exposes a substantial portion of the appliance, and particularly the prongs E of the bracket and the arch wire F extending through the bracket. The prongs E, in particular, present a rather harsh, mechanical appearance.

Figure 4:
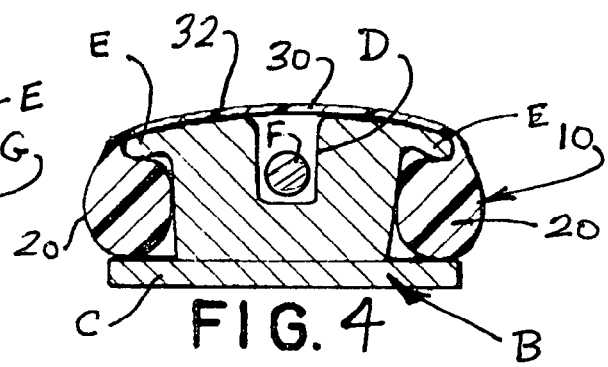
FIG. 4 is a cross-sectional view taken along the line indicated as 4—4 in FIG. 3.
Figure 3:
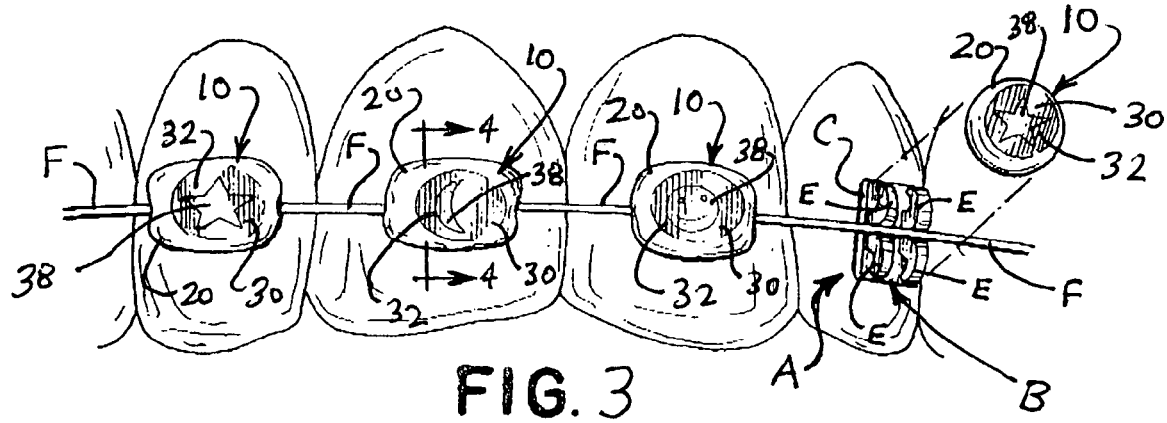
FIG. 3 is a front perspective view showing an arrangement of teeth with the elastomeric orthodontic ligation device shown installed on a conventional orthodontic appliance of the type shown in FIG. 1, wherein the elastomeric ligation device replaces the use of prior art O-rings.

Referring now to the remaining drawing figures, and initially FIGS. 3 and 4, the elastomeric ligation device of the present invention is shown and generally indicated as 10. As seen in FIGS. 3 and 4, the ligation device 10 is specifically adapted to be fastened to the prongs E of the bracket B of the prior art orthodontic appliance A, in the same general manner as the prior art O-rings G. The ligation device 10 is formed entirely of an elastomeric material, such as latex, and includes an O-ring portion 20 and an integral membrane 30. The O-ring portion 20 is adapted to stretch over the hook shaped projections E on the brackets B of the orthodontic appliance A, as shown in FIGS. 3 and 4, for producing a continually acting tractive force that urges the arch wire F against the bracket B in the same manner achieved with the prior art O-ring G shown in FIGS. 1 and 2. The membrane 30 extends across and covers the open area within the inner diameter of the O-ring portion 20. The inner diameter is defined by the maximum straight line distance between an inner circumferential surface 22 of the O-ring portion. The diameter of the membrane 30 is equal to or less than the outer most diameter of the O-ring portion 20, defined across the maximum distance of an outer circumferential surface, 24, so that when the O-ring portion is secured to the bracket, the membrane is pulled tight to cover the prongs E of the bracket and the arch wire F within the slot D of the bracket, as seen in FIG. 3. When the ligation device 10 is fastened to the bracket B, the outer face 32 of the membrane 30 is visibly exposed while the entire bracket B is essentially concealed from view.

Referring to FIG. 5, a top plan view of the ligation device 10 shows the front face 32 of the membrane 30 and the outer diameter of the O-ring portion 20. In this embodiment, the membrane 30 is flat, with no sag or slack when in the relaxed state. The material of the ligation device 10 provides sufficient elasticity to permit stretching of the membrane 30, as well as the O-ring portion 20, over and around the hook shaped projections E of the bracket B as seen in FIG. 4. The cross-section in FIG. 7 illustrates the relatively thin membrane 30 in relation to the thicker cross-section of the O-ring portion 20, with the outermost diameter of the O-ring portion being greater than the diameter of the membrane. This allows the ligation device 10 to be stretched and pulled tight over the hook shaped projections E of the brackets B without excess material or an overhanging lip on the sides of the bracket, thereby avoiding the tendency of plaque to become lodged within any crevice of the oral cavity. Specifically, any excess material or exterior lip extending beyond the bracket B would create an undesirable crevice between the tooth enamel and the ligation device, creating an area which would promote the accumulation of plaque that may be difficult to remove while brushing.

FIG. 6 illustrates an alternative embodiment of the ligation device and is generally indicated as 10A. In particular, the ligation device 10A in FIG. 6 provides for a dimple or sag 36 in the membrane 30 when in the relaxed state. This dimple or sag 36 allows for stretching of the membrane 30 over the hook shaped projections E of the bracket B in the manner shown in FIG. 4, while reducing the tendency of tearing or puncturing of the membrane 30 when stretched across and about the edges of the prong projections E of the bracket B. The cross-section in FIG. 8 illustrates the dimple or sag 36 of the membrane in the relaxed state.

As described above in connection with FIG. 3, the outer face 32 of the membrane 30 is visibly exposed when the ligation device 10, 10A is secured to the bracket B of the orthodontic appliance A. Similar to the O-rings G in the prior art, the ligation device 10, 10A is provided in multiple colors to suit the patients preference. Additionally, any of various designs 38 may be applied to the exposed front face 32 of the membrane 30 to provide a more aesthetically appealing and fashionable appearance. Examples of designs 38 on the face of the membrane are shown in FIGS. 3 and 9–11, and may include a star, half-moon, smiley face or any other design, logo or indicia which would be visible when worn on the orthodontic appliance. Other examples of designs include corporate logos, sports team logos and school logos. The applied design or logo is preferably in a contrasting color to a remainder of the ligation device to enhance the visibility of the design. Moreover, the contrasting colors can be team or school colors which correspond with the logo on the membrane.

While the present invention has been shown and described in accordance with a preferred and practical embodiment thereof, it is recognized that departures from the instant disclosure are contemplated within the spirit and scope of the present invention.

What is claimed is:

1. An orthodontic ligation device for attachment to a bracket that is fixed to a patient's tooth in an orthodontic appliance, said ligation device comprising:
    an integrally formed elastomeric body including;
        an O-ring portion having an outermost diameter and an inner diameter measured between an inner circumferential surface surrounding an open area;
        a membrane spanning across a front tangential plane of the O-ring portion and covering the open area;
        said membrane having a diameter that is less than the outermost diameter of the O-ring portion and greater than the inner diameter of the O-ring portion; and
        said membrane having an outer face that is visibly exposed when the ligation device is attached to the bracket of the orthodontic appliance.

2. The ligation device as recited in claim 1 wherein the integrally formed elastomeric body is provided in any one of a plurality of colors.

3. The ligation device as recited in claim 2 wherein the O-ring portion is of a first color and the membrane is of a second color.

4. The ligation device as recited in claim 1 wherein the integrally formed elastomeric body is of a plurality of colors.

5. The ligation device as recited in claim 1 further comprising:
    a design element applied to the outer face of the membrane.

6. The ligation device as recited in claim 1 wherein the O-ring portion and the membrane are cooperatively structured and disposed to cover the bracket to thereby conceal the bracket from view when the ligation device is attached to the bracket.

7. An orthodontic ligation device for attachment to a bracket that is fixed to a patient's tooth in an orthodontic appliance, said ligation device comprising:
    an integrally formed elastomeric body including:
        an O-ring portion having an outermost diameter and an inner diameter measured between an inner circumferential surface surrounding an open area;
        a membrane spanning across a front tangential plane of the O-ring portion and covering the open area;
        said membrane having a diameter that is not greater than the outermost diameter of the O-ring portion, and the diameter of said membrane being greater than the inner diameter of the O-ring portion; and
        said membrane having an outer face that is visibly exposed when the ligation device is attached to the bracket of the orthodontic appliance.

8. The ligation device as recited in claim 7 wherein the integrally formed elastomeric body is provided in any one of a plurality of colors.

9. The ligation device as recited in claim 7 wherein the integrally formed elastomeric body is of a plurality of colors.

10. The ligation device as recited in claim 9 wherein the O-ring portion is of a first color and the membrane is of a second color.

11. The ligation device as recited in claim 7 further comprising:
    a design element applied to the outer face of the membrane.

12. The ligation device as recited in claim 7 wherein the O-ring portion and the membrane are cooperatively structured and disposed to cover the bracket to thereby conceal the bracket from view when the ligation device is attached to the bracket.

* * * * *